United States Patent [19]

Dietze et al.

[11] 4,177,261

[45] Dec. 4, 1979

[54] PHARMACEUTICAL COMPOSITION AND METHOD OF STIMULATING BLOOD CIRCULATION AND WOUND HEALING

[75] Inventors: Günther Dietze; Matthias Wicklmayr, both of Munich, Fed. Rep. of Germany

[73] Assignee: Thera Gesellschaft für Patentverwertung mbH, Herrsching, Fed. Rep. of Germany

[21] Appl. No.: 865,912

[22] Filed: Dec. 30, 1977

[30] Foreign Application Priority Data

Jan. 3, 1977 [DE] Fed. Rep. of Germany ....... 2700043

[51] Int. Cl.² ...................... A61K 35/14; A61K 37/42
[52] U.S. Cl. ..................................... 424/101; 424/177
[58] Field of Search ................................ 424/101, 177

[56] References Cited

U.S. PATENT DOCUMENTS

2,912,359  11/1959  Anigstein et al. .................... 424/101

FOREIGN PATENT DOCUMENTS

1949195  7/1970  Fed. Rep. of Germany .......... 424/101

OTHER PUBLICATIONS

Chem. Abst., vol. 59, pp. 4334-4335 (1963), No. 4334h.
Chem. Abst., vol. 67, p. 8279 (1967), No. 88107g.
Chem. Abst., vol. 68, p. 3534 (1968), No. 86428p.

*Primary Examiner*—Albert T. Meyers
*Assistant Examiner*—H. Steven Seifert
*Attorney, Agent, or Firm*—Burns, Doane, Swecker & Mathis

[57] ABSTRACT

There is disclosed a pharmaceutical composition useful in stimulating blood circulation and healing of wounds. This composition comprises (a) albumin-freed calf blood extract, and (b) from about 0.001 to about 2.5 micrograms of at least one kinin per milligram of dry extracted substance. A method for treating patients in order to stimulate their blood circulation is also disclosed. This method comprises treating these patients with an effective amount of the pharmaceutical composition described above.

6 Claims, No Drawings

PHARMACEUTICAL COMPOSITION AND METHOD OF STIMULATING BLOOD CIRCULATION AND WOUND HEALING

BACKGROUND OF THE INVENTION

1. Field of the Invention

This invention generally relates to pharmaceutical compositions and methods of treating patients. More specifically, this invention relates to a method for treating patients and a pharmaceutical composition which is useful in stimulating blood circulation and in healing wounds.

2. Description of the Prior Art

The substances that are extracted from albumin-freed blood of young calves, are known to be useful in treating poorly healing wounds, and improving the blood circulation of the tissue, thereby facilitating the healing of the wound. Such substances are also employed for disorders of the cerebellar blood circulation and metabolism. In this connection, see Schnelle, "Medizinische Welt," Volume 19 (1968), page 198. This substance is commercially available under the trade name "Actihaemyl" and is distributed by the Hormonchemie Company in Munich. It may be infused intravenously or intra-arterially, injected intramuscularly or applied locally in the form of an ointment.

It has not yet been determined which substances of the albumin-freed blood serum are responsible for this specific effect. The active substances present in the extract apparently influence also the glucose metabolism according to a report by Mohnicke, et al in "Arzneimittel-Forschung," Volume 18 (1968), page 1021. These authors observed an activation of the oxidizing glucose degradation and an intensification in the build-up of pyruvic acid. Bachmann, et al further report an insulin-like effect on the carbohydrate metabolism. In this connection, see Arzneimittel-Forschung, Volume 18 (1968), page 1023.

However, when the extract obtained from albumin-freed blood of calves is administered for a longer period of time, incidences of incompatibility occur and lead to complications such as anaphylactic shocks, irritations, etc., especially for patients who are subject to allergies. Thus, it is often necesary to discontinue its use.

The search has continued for new pharmaceutical compositions and methods for treating patients in order to stimulate blood circulation. This invention was made as a result of that search.

OBJECTS AND SUMMARY OF THE INVENTION

Accordingly, a general object of the present invention is to avoid or substantially alleviate the above problems of the prior art.

A more specific object of the present invention is to provide a pharmaceutical composition which is useful in stimulating the blood circulation.

A further object of the present invention is to provide a method of treating patients in order to stimulate the blood circulation.

Other objects and advantages of the invention will become apparent from the following summary and description of the preferred embodiments of the present invention.

In one aspect, the present invention provides a pharmaceutical composition useful for stimulating blood circulation and for healing wounds. This composition comprises (a) albumin-freed calf blood extract, and (b) from about 0.001 to about 2.5 micrograms of at least one kinin per milligram of dry extracted substance.

In another aspect, the present invention provides a method of stimulating the blood circulation and healing the wounds of patients. This method comprises treating the patients with an effective amount of the pharmaceutical composition described above.

DESCRIPTION OF THE PREFERRED EMBODIMENTS

Unexpectedly it was found that the admixture of at least one kinin to the extract from albumin-freed blood of calves results in a significant activation of the effective substances contained therein, making it possible to reduce the quantity required for treatment, therefore also reducing the potential danger of complications due to allergies.

According to the present invention, a novel pharmaceutical composition is provided which is intended to improve and stimulate the blood circulation and the healing of wounds. This composition contains, in addition to the substances extracted from the albumin-freed blood of calves, kinins, such as Brady kinin and kallidin, in an amount of from about 0.001 to about 2.5 milligrams per 1 gram of dry extract. These kinins are oligopeptides having from 9 to 11 amino acid units. The nonapeptide Bradykinin has the amino acid sequence ($NH_2$) arginine-proline-proline-glycine-phenylalanine-serine-proline-phenylalanine-arginine (COOH). The decapeptide kallidin is extended at the amino end by an additional lysine radical. The meth-lys-Bradykinin is further extended by a methionine radical.

The kinins are substances which have a kallikrein-like vasodilatoric effect on the blood circulation, cause the relaxed musculary system to contract, and evoke vehement local pain reactions when injected sub-cutaneously, even in minimum quantities. In this connection, see Werle, "Angewandte Chemie," (1961), pages 689 to 720; "Arzneimittel," Volume 1, Verlag Chemie (1968), pages 876 to 880, and Lewis, Handbook of Experimental Pharmacology, Volume XXV [Erdos Springer, New York (1970)], pages 516 to 530.

Kinins, such as Bradykinin and kallidin, are also known to intensify the mobility of spermatozoa and are, therefore, recommended as means to increase fertility, for example, by artificial insemination. In this connection, see published German Application No. 2,357,507.

Kinins are natural products which result from the break-up of certain proteins, which are known as kininogenes and which are formed by the fermentative effect of the kallikrein. Since their structure is now known, they may be produced easily by chemical synthesis from the amino acids.

The intensifying effect of the kinins on the peripheral and the cerebellar blood circulation, and thus the improved healing of wounds, caused originally by the albumin-freed blood extracts, is unexpected. According to prior research, these substances should actually cause an increase in the blood sugar because they promote the passage of the glucose from food dissolved within the intestine into the circulating blood. In this connection, see Meng, et al, "Kininogenases and Kallikrein," [Schattauer, New York (1973)] pages 75 to 80, as well as Moriwaki, et al, "Kalinogenase and Kallikrein" [Schattauer, New York (1975),] pages 57 to 62. It is, therefore, unexpected that the kinins would intensify the healing effects of blood extract, especially when treating ulcers caused by diabetes.

It is further surprising that the composition of the present invention may be easily tolerated by a patient since the intra-cuticular injection of the Brady kinin or kallidin causes vehement pain reactions, even in quantities of only about 0.1 micrograms per 1 milliliter of solution.

In spite of the relatively large amount of kinin which is combined with the substances of the blood extract, such pain reactions are not observed when solutions of the composition of the present invention are administered by injection or infusion, or when the composition is applied locally to the tissue of the wound.

For intra-cutaneous applications particularly, it is expected that the medication containing kinins when used for the treatment of wounds would, of necessity, cause painful reactions in view of the known pain-producing effect of the kinins. However, this is not the case for the concentrations which are useful in the present invention.

Since a smaller amount of albumin-freed blood extract is required when the novel pharmaceutical composition of the present invention is administered, the danger of any production of antibodies and a resulting allergic reaction is substantially reduced. Glucose assimilation by the tissue is intensified by the admixture of kinins, and the reaction of the tissue to the active substances of the extract from the blood of calves is improved, thereby speeding up the healing process. The metabolism of the tissue affected by ulcers which are caused by diabetes is particularly improved, and the healing process significantly accelerated, when the composition of the present invention is employed.

When the pharmaceutical composition of the present invention is prepared for administration by injection or infusion, it may contain, in addition to the kinins and the albumin-freed blood extract, other known additives such as glucose, mineral salts, sodium-lactate and the like. Ointments prepared in accordance with the present invention include, in addition to the kinins, bactericidal substances, such as non-resorbing antibiotics.

The test described hereinbelow demonstrates the effectiveness of the pharmaceutical composition of the present invention.

If a skin defect develops on the leg of a diabetic and the leg has insufficient blood circulation because of peripheral vascular occlusions, healing does not usually take place because the tissue involved cannot assimilate a sufficient amount of glucose to furnish the energy required to rebuild the tissue. This failure of substratum assimilation becomes apparent if the concentration of glucose in the femoral artery and vein of the effected leg is measured by the method proposed by Wahren, et al in "J. Clin. Invest." 51, pages 1870 to 1878 (1972). Flow through the leg is recorded with the aid of a vein closing plethysmograph, as described by Whitney in J. Physiol. (Lond.) 121, pages 1 to 9 (1953).

Five diabetics, who were suffering from multiple vascular occlusions and skin defects of one leg, were given infusions into the femoral artery for a period of 40 minutes with the infusion solution described in Example 4 (100 milliliters containing 100 milligrams of blood extract, 0.230 grams of NaCl and 1 microgram of Bradykinin). After another 20 minutes, i.e., one hour after the beginning of the test, the patients were given another infusion in the same manner as described above, but a control solution was used in the latter case. The control solution is the same as Example 4 but without any kinin.

The results of the measurements of the blood circulation and of the glucose utilization at the beginning and at the end of the specific test periods and the specific solutions used are listed in the Table below in the form of statistical average values ± SEM.

TABLE

The flow of blood and glucose utilization were measured during intra-arterial infusion in the legs of patients who had insufficient blood circulation. These patients each had a diabetic metabolism.

TABLE

| Infusion Solution Used | | Initial Value | 10 minutes | 30 Minutes | 40 Minutes |
|---|---|---|---|---|---|
| Example 4 (with kinin) | Flow of blood (in ml/100g. tissue/min) | 3.82 ± 0.35 | — | — | 8.74 ± 0.36$^a$ |
| | Glucose Utilization (in micromoles/100g. tissue/min) | 0.65 ± 0.13 | 1.72 ± 0.20$^a$ | 2.21 ± 0.19$^a$ | — |
| After One Hour | | | | | |
| Control Solution (without kinin) | Flow of blood (in ml/100g. tissue/min) | 3.56 ± 0.28 | — | — | 4.11 ± 0.24$^{a,b}$ |
| | Glucose Utilization (in micromoles/100g. tissue/min) | 0.75 ± 0.10 | 0.85 ± 0.17$^b$ | 0.95 ± 0.20$^{a,b}$ | — |

The statistical evaluation was performed in accordance with the "Student-T" test, whereby "a" denotes significance in comparison with basic value (p 0.05; paired t-test) and "b" denotes significance in comparison with the prior test (0.05; unpaired t-test).

These tests demonstrate a large increase in the flow of blood from an initial value of 3.82±0.35 to 8.74±0.36 and a distinct improvement in the glucose utilization from 0.65±0.13 micromoles per 100 grams of tissue per minute to 2.21±0.19 micromoles per 100 grams of tissue per minute. When the same test was carried out one hour later, using the same patients but employing a control solution without Bradykinin, only a slight increase in the flow of blood from 3.56±0.28 to 4.11±0.24 and in the glucose utilization from 0.75±0.10 to 0.95±0.20 micromoles per 100 grams of tissue per minute (after 30 minutes) was realized.

The test therefore demonstrates that when a kinin is added to a solution containing blood-extract, there is a significant improvement in the flow of blood through, and the glucose utilization by, the tissue affected.

The present invention is further illustrated by the following examples. All parts and percentages in the examples as well as in the specification and claims are by weight unless otherwise specified.

EXAMPLE 1

Four hundred milligrams of blood-extract (blood extract which has been deproteinized and dried) and 100 micrograms of Bradykinin are mixed with 100 grams of a celluloseglycolate propyleneglycol-jelly base. The jelly so obtained is used for external application for open skin defects.

EXAMPLE 2

One hundred milligrams of blood extract (blood extract which has been deproteinized and dried) and 400 micrograms of Bradykinin are mixed with 100 grams of a polyethylene-glycol-cetylalcohol base. The creme so obtained is used for external application in case of non-wetting skin injuries.

EXAMPLE 3

Five hundred milligrams of blood extract (blood extract which has been deproteinized and dried), 1.4 grams of NaCl and 40 micrograms of Bradykinin are dissolved in water (pro injectione ad 250). The solution is used for intravenous infusion, for an infusion time of about 30 minutes.

EXAMPLE 4

One hundred milligrams of blood extract (blood extract which has been deproteinized and dried), 0.5 grams of NaCl and 1 microgram of Bradykinin are dissolved in water (pro injectione ad 100). The solution so obtained is used for intra-arterial infusion.

EXAMPLE 5

Bradykinin and pulverized blood extract (blood extract which has been deproteinized and dried) are mixed with a pill base-mass consisting of substantially equal parts of agar-agar, calcium carbonate and talcum at a ratio such that 100 milligrams of blood extract and 150 micrograms of Bradykinin are contained in each pill. The pills have a mass of 0.5 grams each. With a dosage of 3–6×1 pills distributed throughout the day, it is possible to significantly lessen the pain of patients who are affected with blood circulation disorders of the heart, brain or extremities.

When the composition of the present invention is to be used in solution form, there is employed from about 10 milligrams to about 1000 milligrams of dry substances and from about 0.1 to about 100 micrograms of at least one kinin per 100 milliliters of solution.

When the compositions of the present invention is in the form of an ointment, jelly or creme for the local treatment of wounds, the composition contains from about 0.1 to about 10 milligrams of dry extracted substances and from about 0.1 to about 100 micrograms of kinin per 1 gram of ointment, jelly or creme.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

We claim:

1. A pharmaceutical composition useful for improving and stimulating blood circulation and thereby improving the healing of wounds, said composition comprising (a) albumin-freed calf blood extract, and (b) from about 0.001 to about 2.5 micrograms of a kinin selected from the group consisting of Brady kinin and kallidin per milligram of dry albumin-freed calf blood extract.

2. The composition of claim 1, wherein said composition is in solution form and comprises from about 100 milligrams to about 1000 milligrams of dry albumin-freed calf blood extract and from about 0.1 to about 100 milligrams of kinin per 100 milliliters of solution.

3. A pharmaceutical composition useful for improving and stimulating blood circulation and thereby improving the healing of wounds, said composition being in the form of an ointment, jelly, or creme and comprising (a) 0.1 to about 10 milligrams of albumin-freed calf blood extract, and (b) from about 0.1 to about 100 micrograms of a kinin selected from the group consisting of Brady kinin and kallidin per 1 gram of ointment, jelly or creme.

4. A method for treating patients to improve the blood circulation and thereby improve the healing of wounds, said method comprising administering to said patients an effective amount of a composition comprising (a) albumin-freed calf blood extract, and (b) from about 0.001 to about 2.5 micrograms of a kinin selected from the group consisting of Brady kinin and kallidin per milligram of dry albumin-freed calf blood extract.

5. The method of claim 4, wherein said composition is in solution form and comprises from about 10 milligrams to about 1000 milligrams of dry albumin-freed calf blood extract and from about 0.1 to about 100 micrograms of kinin per 100 milliliters of solution.

6. A method for treating patients to improve the blood circulation and thereby improve the healing of wounds, said method comprising externally administering to said patients an effective amount of a composition in the form of an ointment, jelly, or creme and comprising (a) from about 0.1 to about 10 milligrams of albumin-freed calf blood extract, and (b) from about 0.1 to about 100 micrograms of a kinin selected from the group consisting of Brady kinin and kallidin per 1 gram of ointment, jelly or creme.

* * * * *